United States Patent [19]

Pirzada et al.

[11] Patent Number: 5,851,507
[45] Date of Patent: Dec. 22, 1998

[54] INTEGRATED THERMAL PROCESS FOR THE CONTINUOUS SYNTHESIS OF NANOSCALE POWDERS

[75] Inventors: Shahid Pirzada; Tapesh Yadav, both of Tucson, Ariz.

[73] Assignee: Nanomaterials Research Corporation, Longmonte, Colo.

[21] Appl. No.: 706,819

[22] Filed: Sep. 3, 1996

[51] Int. Cl.[6] ............................ B22F 9/00; C01B 21/072; C01B 13/14; C01B 21/30

[52] U.S. Cl. .............................. 423/659; 75/343; 75/351; 423/289; 423/345; 423/409; 423/412; 423/439; 423/440; 423/592; 423/606

[58] Field of Search .................................. 423/412, 592, 423/409, 439, 440, 659, 606, 345, 289; 75/343, 351

[56] References Cited

U.S. PATENT DOCUMENTS

| | | | |
|---|---|---|---|
| 4,484,943 | 11/1984 | Miura et al. | 423/412 |
| 4,588,575 | 5/1986 | David | 423/592 |
| 4,610,857 | 9/1986 | Ogawa et al. | 423/412 |
| 4,721,610 | 1/1988 | Yoshida et al. | 423/592 |
| 4,842,832 | 6/1989 | Inoue et al. | 423/592 |
| 4,851,262 | 7/1989 | McFeaters | 423/412 |
| 5,417,956 | 5/1995 | Moser | 423/592 |
| 5,447,708 | 9/1995 | Helble et al. | 423/592 |
| 5,472,477 | 12/1995 | König | 423/440 |

FOREIGN PATENT DOCUMENTS

| | | | |
|---|---|---|---|
| 102110 | 4/1990 | Japan | 423/412 |
| 1654258 | 6/1991 | Russian Federation | 423/412 |

OTHER PUBLICATIONS

H. Gleiter, "Mechanical Properties and Deformation Behavior of Materials Having Ultra–Fine Microstructures," Nastasi et al. Ed., 3–35 (1993).
R. W. Siegel, "Mechanical Properties and Deformation Behavior of Materials Having Ultra–fine Microstructures," Nastasi et al. Ed., 509 (1993).
Nieman et al., "J. Mater. Res.," 6, 1012 (1991).
Nieman et al., "Scripta Metall. et Mater.," 24, 145 (1990).
Skandon et al., "Scripta Metall. et Mater.," 25, 2389 (1991).
Eastman et al., "Mater. Res. Soc. Symp. Proc.," 155, 255 (1989).
H. Hahn et al., "Mater. Res. Soc. Symp. Proc.," 196, 71 (1990).
M. J. Mayo, Mechanical Properties and Deformation Behavior of Materials Having Ultra–fine Microstructures, 361 (1993).
Beck and Siegel, "J. Mater. Res.," 7, 2840 (1992).
Tamaki et al., "J. Electrochem. Soc.," 141, 2207 (1994).
Sugaya et al., IEEE Trans. on Magnetics, 31, 2197 (1995).
Yeack–Scranton, "Nanomagentism," Kluwer Academic, Netherland, 1–6 (1993).
Steigerwald and Brus, "Ann. Rev. Mater. Sci.," 19, 471 (1989).
R. Uyeda, "Prog. Mater. Sci.," 35, 1 (1991), and R. W. Siegel, Materials Science and Technology, 15, VCH, Weinhem, 583 (1991).
G. S. Springer, "Advances in Heat Transfer," 14, 281–341, Academic Press (1978).
S. Iwama et al, "Ultrafine Powders of TiN and AlN Produced by a Reactive Gas Evaporation Technique with Electron Beam Heating," *Journal of Crystal Growth* 56 (1982) 265–269, North–Holland Publishing Company.

*Primary Examiner*—Wayne Langel
*Attorney, Agent, or Firm*—Choate, Hall & Stewart

[57] ABSTRACT

A continuous process that produces nanoscale powders from different types of precursor material by evaporating the material and quenching the vaporized phase in a converging-diverging expansion nozzle. The precursor material suspended in a carrier gas is continuously vaporized in a thermal reaction chamber under conditions that favor nucleation of the resulting vapor. Immediately after the initial nucleation stages, the vapor stream is rapidly and uniformly quenched at rates of at least 1,000 K/sec, preferably above 1,000,000 K/sec, to block the continued growth of the nucleated particles and produce a nanosize powder suspension of narrow particle-size distribution. The nanopowder is then harvested by filtration from the quenched vapor stream and the carrier medium is purified, compressed and recycled for mixing with new precursor material in the feed stream.

25 Claims, 15 Drawing Sheets

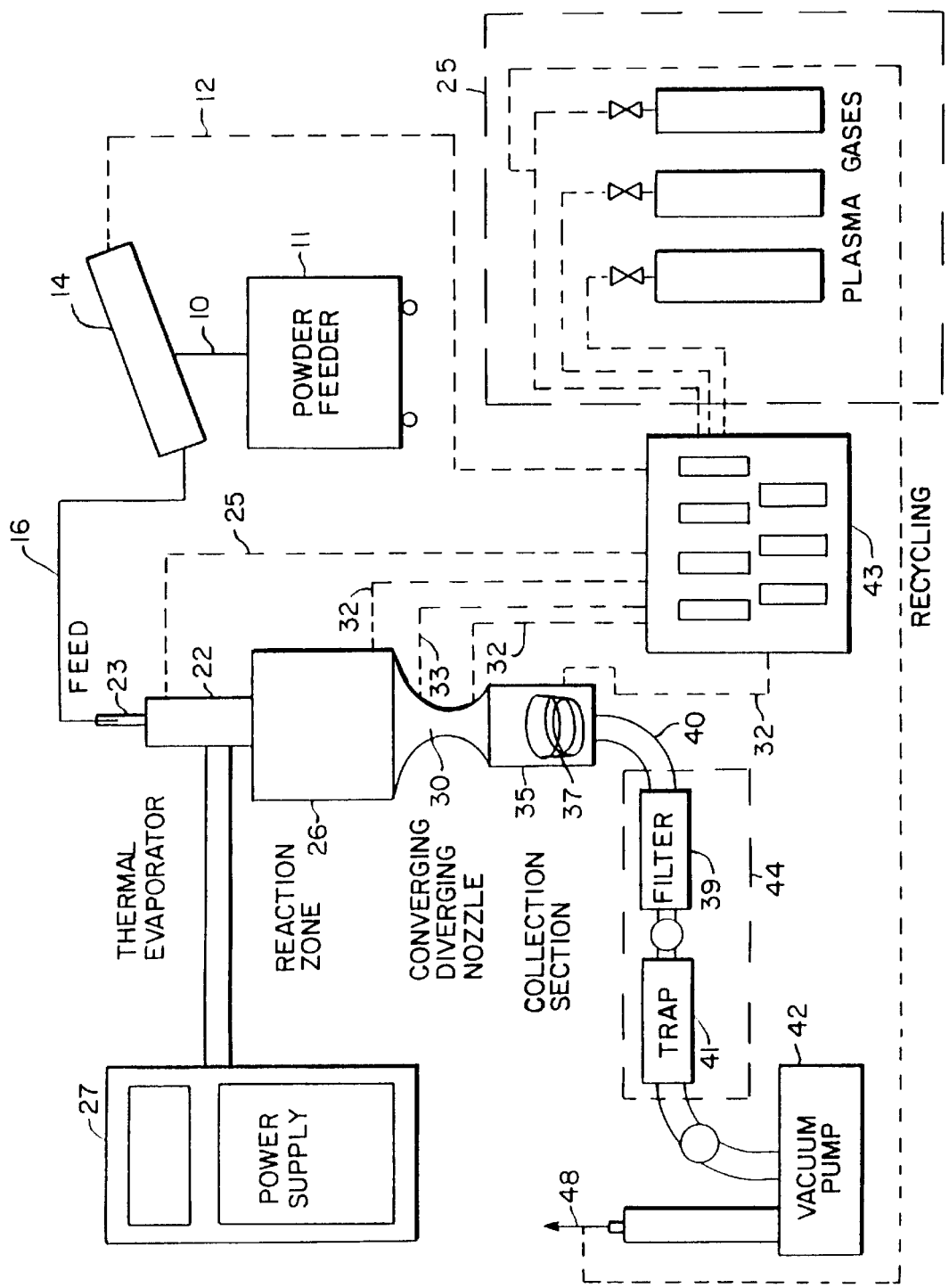

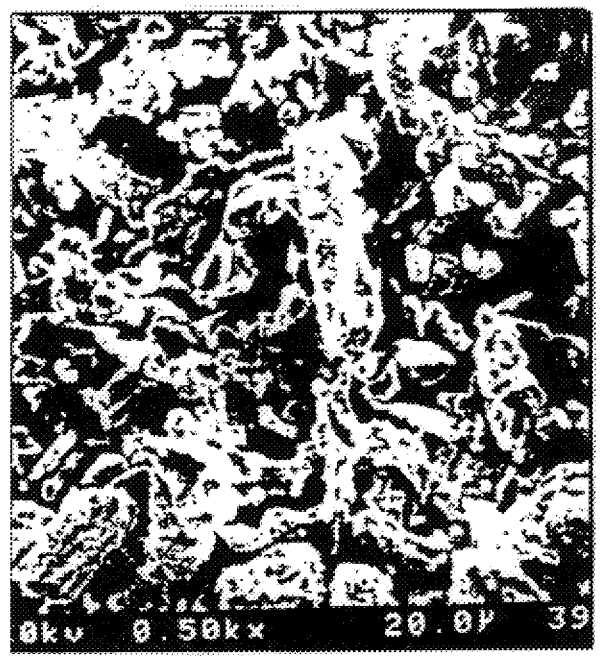
Titanium
FIG. 6
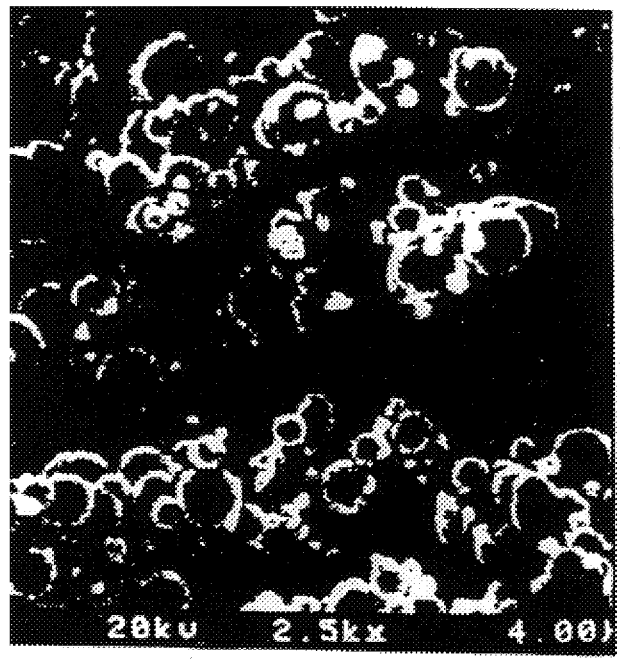
Iron

INTEGRATED THERMAL PROCESS FOR THE CONTINUOUS SYNTHESIS OF NANOSCALE POWDERS

BACKGROUND OF THE INVENTION

1. Field of the Invention

This invention pertains in general to processes for the synthesis of submicron particles. In particular, the invention relates to a novel approach utilizing vaporization and ultra-rapid thermal quenching by adiabatic expansion to produce submicron particles under controlled operating conditions.

2. Description of the Prior Art

As defined in the art, submicron powders are materials having average grain size below 1 micrometer. Of particular interest are nanoscale powders; namely, submicron powders with grain size less than 100 nanometers and with a significant fraction of interfacial atoms. It is known that within these size ranges a variety of confinement effects occur that dramatically change the properties of the material. A property will be altered when the entity or mechanism responsible for that property is confined within a space smaller than some critical length associated with that entity or mechanism. See H. Gleiter, *Mechanical Properties and Deformation Behavior of Materials Having Ultra-Fine Microstructures,* Nastasi et al. Ed., 3–35 (1993); and R. W. Siegel, *Mechanical Properties and Deformation Behavior of Materials Having Ultra-fine Microstructures,* Nastasi et al. Ed., 509 (1993). Thus, for example, a normally ductile metal will become significantly harder if its grain size is reduced to the point where moving dislocations through its crystal lattice are no longer able to occur at normal levels of applied stress. Since the stress required to produce a Frank-Read dislocation is inversely proportional to the spacing between its pinning points, as one skilled in the art would readily understand, a critical length in this case is that for which the stress necessary to produce a dislocation becomes larger than the conventional yield stress for the given metal.

Thus, confinement effects can be exploited to produce extremely hard and strong materials with much higher yield stress than exhibited by the conventional form of their precursors. See Nieman et al., "Mechanical Behavior of Nanocrystalline Cu and Pd," J. Mater. Res., 6, 1012 (1991); and Nieman et al., "Tensile Strength and Creep Properties of Nanocrystalline Palladium," Scripta Metall. et Mater., 24, 145 (1990). The same principle has also been used to manufacture unique optical materials with grain sizes tailored for excitonic interactions with particular wavelengths, Skandon et al., "Nanostructured $Y_2O_3$: Synthesis and Relation to Microstructure and Properties," Scripta Metall. et Mater., 25, 2389 (1991); electroceramics with unique electronic and electrical characteristics, Eastman et al., "Processing and Properties of Nanophase Oxides," Mater. Res. Soc. Symp. Proc., 155, 255 (1989); superplastic ceramics with grain sizes engineered to allow low cost, rapid net-shape forming of ceramics as a substitute process for machining of ceramics, H. Hahn et al., "Low Temperature Sintering and Deformation of Nanocrystalline $TiO_2$," Mater. Res. Soc. Symp. Proc., 196, 71 (1990) and M. J. Mayo, *Mechanical Properties and Deformation Behavior of Materials Having Ultra-fine Microstructures,* Nastasi et al. Ed., 361 (1993); catalysts with extremely high surface areas, high selectivity and activity, Beck and Siegel, "The Dissociative Adsorption of Hydrogen Sulfide over Nanophase Titanium Dioxide," J. Mater. Res., 7, 2840 (1992); materials with unique electrochemical properties, Tamaki et al., "Grain-Size Effects in Tungsten Oxide-Based Sensor for Nitrogen Oxides," J. Electrochem. Soc., 141, 2207 (1994); and materials that exhibit unprecedented magnetic properties, Sugaya et al., "Soft Magnetic Properties of Nano-Structure-Controlled Magnetic Materials," IEEE Trans. on Magnetics, 31, 2197 (1995) and C. E. Yeack-Scranton, *Nanomagnetism,* Kluwer Academic, Netherland, 1–6 (1993). In view of these results, submicron powders in general, and nanoscale powders (nanopowders) in particular, represent an extraordinary opportunity for designing and developing a wide range of structural, optical, electrical, electronic, electrochemical, magnetic and chemical applications.

Although this opportunity has been apparent for several years, large scale commercialization has remained unrealized because of the high cost and low throughput of existing processes for producing nanopowders, the current lack of process control over size and size distribution of the resulting material, the unpredictable composition of its constituent phases, and the lack of control over the nature of and the interactions among the interfaces created between the constituent phases. Nanopowders may indeed represent the threshold of a new era in materials technology, but the key to their full utilization depends on the development of new processes for producing nanopowders economically and in commercially viable quantities under controlled operating conditions.

In recent years, several methods have been used for producing nanopowders and the materials produced by this prior-art technology have confirmed the fact that nanopowders possess important technical properties that show the potential for becoming commercially significant. However, all known production methods consist of batch processes that are too expensive to yield commercially affordable materials for bulk applications (current production costs for these processes are orders of magnitude higher than the $10.00/lb target price considered economical for bulk applications of these materials). Therefore, the commercial future of nanopowders depends on the development of a process that can produce nanopowders with predetermined properties, in commercially viable quantities, and at an affordable cost.

Ideally, the synthesis and processing technology for nanopowders should allow control of the size and size distribution of the constituent structures and phases (this is critical to the mechanistic performance of nanopowders); allow control of the composition of the phases in the nanomaterial (critical to define the property domain of the nanomaterial); and allow control over the nature of interfaces (e.g. purity) and the interaction between interfaces (critical to the interface-based characteristics of the nanopowders). None of the known processes for the synthesis of nanomaterials possesses these characteristics; therefore, none is suitable for bulk commercialization of nanopowders.

In particular, prior-art processes are all batch, and have high energy or solvent processing requirements, which are all inherent limitations to the cost-effective and large-scale production of nanopowders. The processes currently in use can be classified into three general groups: chemical, mechanical-attrition, and gas-condensation methods. The chemical methods include precipitation techniques, sol-gel processes, and inverse-micelle methods. See Beck and Siegel, "The Dissociative Adsorption of Hydrogen Sulfide over Nanophase Titanium Dioxide," J. Mater. Res., 7, 2840 (1992), and Steigerwald and Brus, "Synthesis, Stabilization, and Electronic Structure of Quantum Semiconductor Nanoclusters," Ann. Rev. Mater. Sci., 19, 471 (1989). These processes have been used to successfully synthesize narrowly distributed nanopowders; however, being chemical-media based, the resulting nanopowders are covered with chemical surface layers. This surface covering adversely affects the properties of the nanopowders and inhibits their further processing into bulk materials. In addition, the use of solvents and chemicals has a significant economic impact on the synthesis process because of the costs of chemicals and the pollution remediation required by their use.

The mechanical attrition methods rely on the physical decomposition of coarser grains through severe mechanical deformation. Such processing methods are energy intensive, have low flexibility, are susceptible to contamination by attrition tools or media, and afford little control over the quality and consistency of the final product.

The gas condensation methods essentially involve the evaporation of a coarse (at least micron size) source of precursor material, such as a metal, inorganic, etc., in an inert gas at a low pressure. The evaporated source atoms or molecules collide with the gas atoms or molecules and lose energy, thereby causing a homogeneous condensation of atom or molecule clusters in the supersaturated vicinity of the precursor source. The further accretion and/or coalescence of the nucleated particles is minimized by rapid removal of the nanometer-sized powders so formed from the region of supersaturation. See R. Uyeda, "Studies of Ultrafine Particles in Japan: Crystallography, Methods of Preparation and Technological Applications," Prog. Mater. Sci., 35, 1 (1991), and R. W. Siegel, *Materials Science and Technology*, 15, VCH, Weinheim, 583 (1991). Alternatively, gas condensation processes may involve gas-phase reactions. Some of the known gas condensation processes have produced nanomaterials of acceptable size distribution, but they are all batch operations and are not readily scaleable for commercial exploitation.

Therefore, there continues to be a need for a low-cost process (less than $10/lb) that is suitable for large-scale production of nanopowders under controlled operating conditions. The present invention discloses a pioneering and unique thermal condensation process that satisfies these requirements for the continuous production of nanopowders in bulk quantities.

SUMMARY OF THE INVENTION

One of the objectives of this invention is a low capital-cost process for the production of nanosize powders in bulk quantities.

Another objective of the invention is a process that can be carried out with low utility costs (that is, low energy input, energy output, and maintenance expenses).

Another goal is a process with low operating costs (i.e., labor, recycling, raw materials, plant space, etc.); accordingly, the invention aims at a process with a high yield per pass and high product selectivity.

Another objective is a process that is continuous and suitable for scaling up to production rates in the order of tons per day.

Yet another goal is a process that is simple, easy to operate, and flexible, so as to allow the production of multiple products with relatively simple operating changes.

Still another objective is a process that is safe and environmentally benign.

Finally, another goal is an operationally stable process that requires a minimal external-control structure for steady-state operation.

A process that satisfies most of these features would be very desirable because it would enable the economical manufacture of nanopowders in bulk quantities. Therefore, according to the foregoing objectives, one aspect of the this invention involves the continuous vaporization of commercially-available, coarse precursor material suspended in a carrier gas in a thermal reaction chamber under conditions that minimize superheating and favor nucleation of the resulting vapor. Optionally, a kinetic gas feed may be mixed with the vapor in the reactor to reach a thermokinetic state of the vapor that may be required to produce controlled nucleation of solid powders from the vapor stream. Immediately after the initial nucleation stages, the vapor stream is rapidly and uniformly quenched at rates of at least 1,000K per second, preferably greater than 1,000,000K per second, to block the continued growth of the nucleated particles and produce a nanosize powder suspension of narrow particle-size distribution. The nanopowder is then harvested by filtration from the quenched vapor stream and the carrier medium is purified, compressed and recycled for mixing with new precursor material in the feed stream.

According to another aspect of the invention, the thermal quenching is carried out in a converging-diverging expansion nozzle that exploits the Joule-Thompson principle of adiabatic expansion of high-temperature vapors. The theoretical behavior of the Joule-Thompson adiabatic expansion process is described by the well-known equation:

$$T_2/T_1 = (P_2/P_1)^{(k-1)/k}, \qquad (1)$$

where $T_1$ and $T_2$ are the temperatures before and after expansion, respectively; $P_1$ and $P_2$ are the pressures before and after expansion, respectively; and k is the ratio of the expanding fluid's specific heats at constant pressure and constant volume ($C_p/C_v$).

Applying Equation 1 to a temperature change occurring during adiabatic expansion, $\Delta T$, $$\Delta T/T_1 = (T_2-T_1)/T_1 = (P_2/P_1)^{(k-1)/k} - 1; \qquad (2)$$

or, for a steady state process, $$dT/dt = T_1 \, d[(P_2/P_1)^{(k-1)/k}]/dt. \qquad (3)$$

Equation 3 suggests that Joule-Thompson expansion can quench high-temperature vapors at a steady-state quench rate that depends on the rate at which the pressure is reduced across a given adiabatic expansion device. Thus, in a continuous, steady-state process, the rate can be changed by changing the rate of expansion, which provides a much-sought form of control over the nucleation process of nanopowders produced by vapor condensation. Since it is known that the size, size distribution and other properties of vapor condensation products depend on the speed at which the nucleating material is quenched, the adiabatic expansion approach of the present invention provides an invaluable tool, missing in all prior-art processes, for controlling the quality of the resulting nanopowders. In addition, because the process is stably carried out in continuous fashion, it provides a suitable vehicle for large scale applications and commercial production of bulk nanomaterials.

It is noted that the process of the invention is described in terms of adiabatic conditions because of the principles outlined above. Other aspects of the invention, though, involve cooling of the expansion device utilized to practice the process and the use of a boundary-layer gas blanket to avoid undesirable condensation, thereby improving the process. Therefore, although the preferred embodiment of the process remains substantially adiabatic, it is understood that limited heat transfer in fact occurs at the wall of the expansion device.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIG. 2 is a schematic illustration of a pilot-plant process according to the preferred embodiment of the invention.

FIG. 6 is a scanning electron microscope image of the iron and titanium material used in Example 2, showing that the feed powders were greater than 1 micrometer.

DETAILED DESCRIPTION OF THE INVENTION

A primary aspect of this invention lies in the discovery that the size and size distribution of nanopowders produced by vapor condensation can be controlled by interrupting the growth process through ultra-rapid thermal quenching of the condensing vapor. Another critical aspect of the invention is the realization that Joule-Thompson adiabatic expansion provides a controllable process for quenching such condensing vapor at predetermined rates as high as $10^6$ °C./sec, or greater, as required for producing nanopowders of desired properties. A third, important aspect of the invention is the development of a converging-diverging nozzle to implement the adiabatic expansion process of the invention under predictable conditions for a variety of precursor materials and operating conditions.

Figure 1:
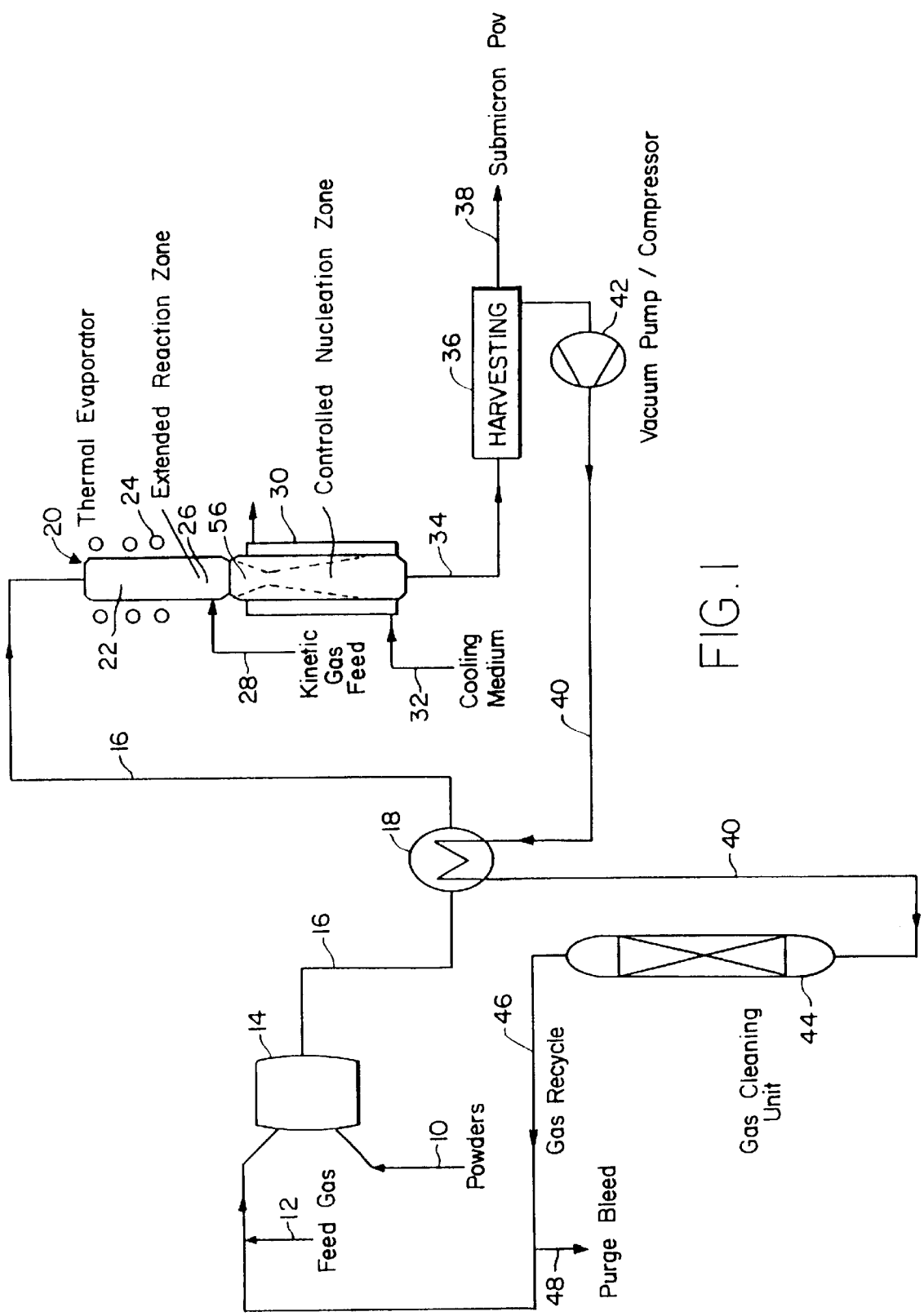
FIG. 1 is a schematic representation of the adiabatic-expansion, thermal quenching process of the present invention.

Referring to the drawings, wherein like parts are designated throughout with like numerals and symbols, FIG. 1 shows the process flow diagram and a schematic representation of the apparatus of the invention as applied to solid precursors, such as metals, alloys, ceramics, composites, and combinations thereof. It is understood that the process applies equivalently to other forms of precursors such as liquid, gaseous, slurry, and combinations thereof. A feed stream 10 of such a precursor material in powder form is premixed with a feed gas stream 12 (such as argon, helium, nitrogen, oxygen, hydrogen, water vapor, methane, air, or a combination thereof, depending on the particular precursor being processed and the corresponding atmosphere—inert, oxidizing, or reducing—required for the process) in mixing apparatus 14 appropriate to create a suspension. The powder 10 is suspended in the gas 12, preferably in a continuous operation, using fluidized beds, spouting beds, hoppers, or combinations thereof, as best suited to the nature of the precursor. The test runs performed to reduce the invention to practice were conducted with precursor feeds having particle size greater than 1 micrometer, but the process could be used with any size suitable for its continuous vaporization in a gas stream. The resulting gas-stream suspension 16 is advantageously preheated in a heat exchanger 18 and then is fed into a thermal reactor 20 where the suspended powder particles are partially or, preferably, completely evaporated in a thermal evaporation zone 22 by the input of thermal energy. The source 24 of such thermal energy may be internal energy, heat of reaction, conductive, convective, radiative, inductive, microwave, electromagnetic, direct or pulsed electric arc, nuclear, or combinations thereof, so long as sufficient to cause the rapid vaporization of the powder suspension being processed. Optionally, in order to prevent contamination of the vapor stream caused by partial sublimation or vaporization of the thermal reactor's interior walls, they may be pre-coated with the same material being processed.

The vaporized gas-stream suspension next enters an extended reaction zone 26 of the thermal reactor that provides additional residence time, as needed to complete the evaporation of the feed material and to provide additional reaction time (if necessary). As the stream leaves the reactor, it passes through a zone 56 where the thermokinetic conditions favor the nucleation of solid powders from the vaporized precursor. These conditions are determined by calculating the supersaturation ratio and critical cluster size required to initiate nucleation. Rapid quenching leads to high supersaturation which gives rise to homogeneous nucleation. The unstable vapor phase system self-nucleates on atomic clusters of critical size. Below the critical size, the clusters are unstable for a given supersaturation, while above the cluster size the free energy of the cluster is negative. For an ideal vapor phase, the radius of the critical cluster size is given by the relation $$r = 2\gamma V/kT\ln(P_1/P_\infty), \quad (4)$$

where $\gamma$ is the surface free energy, V is the molecular volume of the condensed phase, k is Boltzman's constant, $P_1$ is the pressure of the vapor in the system, and $P_\infty$ is the vapor pressure of the condensed phase. See G. S. Springer, *Advances in Heat Transfer*, 14, 281–341, Academic Press (1978).

Using titanium powder as an example, based on the physical properties of the feed material and operating conditions in the reactor (size=10 $\mu$, melting point=1,660° C., boiling point=3,287° C., heat of vaporization of titanium= 10.985 Btu/g, hot gas temperature=4,000° C.), it is possible to calculate the residence time required for vaporization (2.32 msec for heating to melting point, 0.265 msec for melting, 5.24 msec for vaporization; total time required= 8–10 msec). Based on the velocity of the suspension injected into the reactor and the travel distance through the reactor, one can determine that a velocity of about 46 ft/sec produces a residence time of 10.7 msec, sufficient for vaporization. If the process requires a predetermined thermokinetic state of the powder being processed which can be enhanced by the presence of a particular gas, a kinetic gas feed 28 (such as argon, helium, nitrogen, oxygen, hydrogen, water vapor, methane, air, or combinations thereof) can also be mixed with the precursor vapor to reach the desired thermokinetic state. As soon as the vapor has begun nucleation, the process stream is quenched in a converging-diverging nozzle-driven adiabatic expansion chamber 30 at rates at least exceeding $10^3$ K/sec, preferably greater than 106 K/sec, or as high as possible. As further detailed below, a cooling medium 32 is utilized for the converging-diverging nozzle to prevent contamination of the product and damage to the expansion chamber 30. Rapid quenching ensures that the powder produced is homogeneous, its size is uniform and the mean powder size remains in submicron scale.

The quenched gas stream 34 is filtered in appropriate separation equipment 36 to remove the submicron powder product 38 from the gas stream. As well understood in the art, the filtration can be accomplished by single stage or multistage impingement filters, electrostatic filters, screen filters, fabric filters, cyclones, scrubbers, magnetic filters, or combinations thereof. The filtered nanopowder product 38 is then harvested from the filter 36 either in batch mode or continuously using screw conveyors or gas-phase solid transport and the product stream is conveyed to powder processing or packaging unit operations (not shown in the drawings). The filtered gas stream 40 is compressed in a vacuum-pump/compressor unit 42 and cooled by preheating the gas-stream suspension 16 in heat exchanger 18. Thus, the enthalpy of compression can be utilized by the process as process heat through heat integration. Stream 40 is then treated in a gas cleaning unit 44 to remove impurities and any undesirable process product gases (such as CO, $CO_2$, $H_2O$, HCl, $NH_3$, etc). The gas treatment can be accomplished by single stage or multistage gas-gas separation unit operations such as absorption, adsorption, extraction, condensation, membrane separation, fractional diffusion, reactive separation, fractional separation, and combinations thereof. Finally, the treated gases 46 are recycled back to be reused with the feed gas stream 12. A small split stream 48 of the compressed treated gas 46 is purged to ensure steady state operation of the continuous thermal process.

The invention was reduced to practice in a pilot plant illustrated schematically in FIG. 2. This thermal reactor system consists of an upper, cylindrical, thermal evaporation chamber 22 made of quartz and cooled by circulating water (not shown). The gas-stream suspension 16 is formed by mixing the solid feed material 10 fed by a powder feeder 11 with an inert gas stream 12, such as argon. The suspension 16 is injected continuously from the top of the thermal evaporation chamber 22 through a water-cooled injection probe 23 and it is heated inductively by means of an RF plasma torch 24 (consisting of a plasma-gas source 25 and a suitable power supply 27). The reactor also comprises another, cylindrical, extended reaction zone 26 made of stainless steel, water cooled, positioned downstream of the thermal evaporation zone 22, and sufficiently large to give the feed stream the residence time required to complete the vaporization and reaction. The reaction zone 26 is lined with a zirconia refractory felt and a layer of silicon-carbide refractory material to reduce heat losses from the hot reaction zone. If necessary to prevent contamination of the reacting fluid by the reactor or refractory material, the reactor's interior walls (and refractory lining) may be further lined with the same material constituting the solid feed.

Figure 3A:
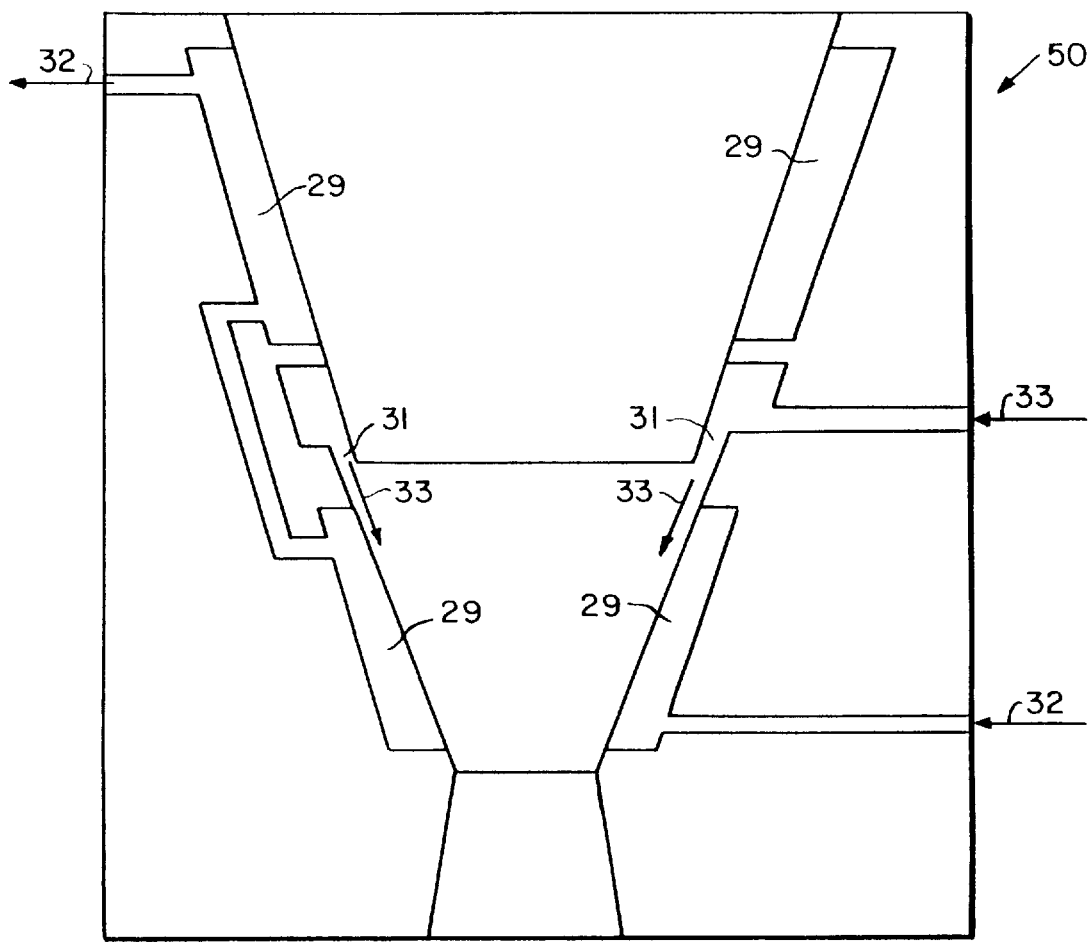
FIG. 3a is a schematic illustration of a converging-diverging expansion nozzle according to the preferred embodiment of the invention.
Figure 3B:
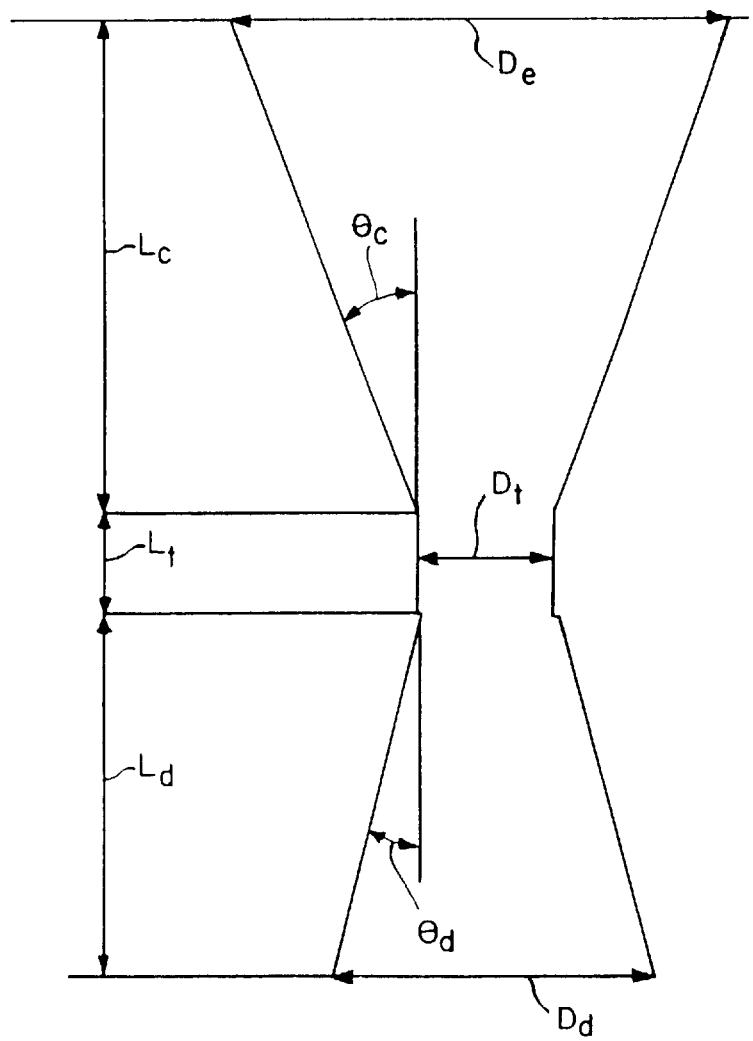
FIG. 3b is a simplified drawing of the expansion nozzle of the invention to illustrate the key design parameters for the process.

The adiabatic expansion chamber 30 consists of a converging-diverging nozzle, as illustrated in FIG. 3a, operated with a pressure drop (created by the vacuum pump 42 operated at 50 to 650 Torr) sufficient for quenching the high-temperature vapors produced by plasma induction upstream in the reactor. A simple schematic of such a converging-diverging nozzle is shown in FIG. 3b to illustrate the key design parameters of the device. They are the diameter $D_c$, the length $L_c$ and the converging angle $\Theta_c$ for the converging section; the diameter $D_d$, the length $L_d$ and the diverging angle $\Theta_d$ for the diverging section; and the diameter $D_t$ and length $L_t$ for the throat. For durability and continuous operation, it is necessary to keep the nozzle wall cool to avoid contamination of the quenched product with the material of construction of the nozzle or, in worst cases, even to avoid melt down and structural failure of the nozzle. Accordingly, the temperature of the nozzle is maintained low with a coolant 32, such as cooling water, circulating in a cooling jacket 29.

In addition, although lower nozzle-wall temperatures improve the contamination and failure problems, such lower temperatures can also lead to vapor condensation on the nozzle walls because of mechanisms such as thermophoresis. Vapor condensation can, in turn, lead to increasing restriction in the nozzle throat diameter, with subsequent closure of the throat and failure of the nozzle. We solved this additional problem by providing a gaseous boundary-layer stream 33 to form a blanket over the internal surface of the nozzle. The blanket gases can be introduced into the nozzle's interior wall axially, radially or tangentially, through an inlet port 31, and can be inert, such as argon or helium when metals and alloys are being processed; or reactive, such as nitrogen, when nitrides are being synthesized; or oxygen or air, when oxides are being processed; methane and hydrocarbons, when carbides are being processed; halogens when halides are being synthesized; or combinations thereof, depending on the ultimate material being synthesized. Thus, reactive gases can participate in heat transfer with the nucleation process, or reactively on powder surface to selectively modify the composition of the surface (coated powders), or reactively to transform the bulk composition of the powder, or in combinations to achieve multiple functions. This secondary gas feed 33 can help engineer the product nucleation process and the resultant characteristics of the powder.

The separation system 36 of the invention is realized by means of a collection chamber 35, attached to the outlet of the nozzle 30, where the very fine particles entrained in the gaseous stream are collected on a water-cooled metallic coil 37 (copper was used successfully for the test runs detailed below) and periodically extracted. It is anticipated that commercial-scale equipment would incorporate a screw or similar conveyor for the continuous removal of the nanopowder product from the collection chamber 35. The gas stream 40 out of the collection chamber is further passed through a filter 39 and trap 41 to thoroughly clean it prior to passage through the vacuum pump 42. A monitor and fluid-control panel 43 is utilized to monitor process variables (temperatures, pressures, water and gas flow rates), record them, and control all water and gas streams to maintain steady-state operation. It is noted that for simplicity the gas stream 48 exhausted from the vacuum pump 42 was not recycled in the demonstration plant of FIG. 2, but a commercial application would preferably do so for energy and material conservation.

The effectiveness of the invention was demonstrated by utilizing the system of FIG. 2 to produce nanosize powders of several different materials. In each case, the powders harvested were characterized for phases, size, morphology, and size distribution. X-ray diffraction (XRD) was used to determine the phases present in the samples using a Siemens D5000 difractometer with Ni-filtered Cu K$\alpha$ radiation. The peak widths for average grain size analysis were determined by a least-square fit of a Cauchy function. The average size of the powder produced was estimated by Scherrer's method. Transmission electron microscopy (Hitachi TEM H-8100 equipped with a Kevex® EDX) was used for size, morphology, and size distribution. The particle size of the powders produced was in the nanometer range. Scanning electron microscopy (SEM) was used for the coarser size feed powders.

EXAMPLE 1

Figure 4:
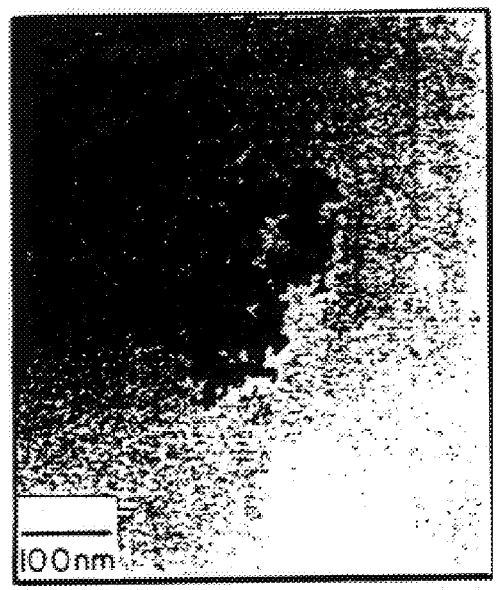
FIG. 4 is a transmission electron microscope image of the zinc nanopowder produced in Example 1.
Figure 5:
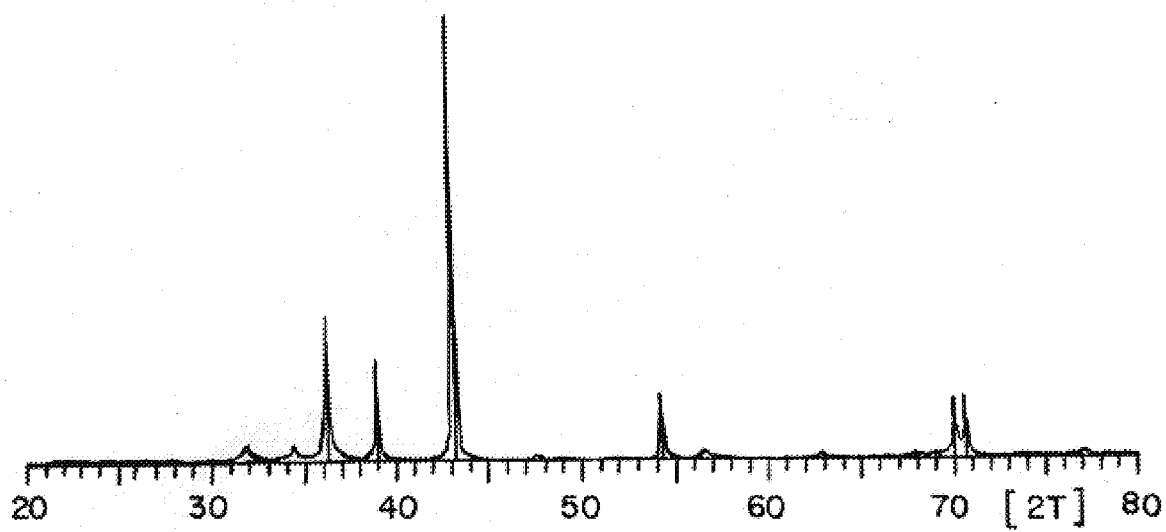
FIG. 5 is an X-ray diffraction pattern of the product of Example 1, indicating that the phase formed was zinc.

Zinc: Commercially available zinc powder (–325 mesh) was used as the precursor to produce nanosize zinc powder. Feed zinc powder was fed into the thermal reactor suspended in an argon stream (argon was used as the plasma gas; the total argon flow rate was 2.5 ft$^3$/min). The reactor was inductively heated with 16 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 4 is the TEM micrograph (or nanograph) of the nanosize powder produced by the invention, showing it to be in the 5–25 nanometer range. The size distribution was narrow, with a mean size of approximately 15 nm and a standard deviation of about 7.5 nm. Variations in the operating variables (such as power input, gas pressure, gas flow rates, and nozzle throat size) affected the size of the powder produced. An XRD pattern of the product is shown in FIG. 5, which indicates that the only phase present was zinc. To avoid condensation at the wall, argon was introduced tangentially (radial or axial injections have also been proven to be effective) at the nozzle walls. The inert gas provided cooling as well as a boundary layer to act as a barrier for any condensation on the nozzle walls.

EXAMPLE 2

Figure 7:
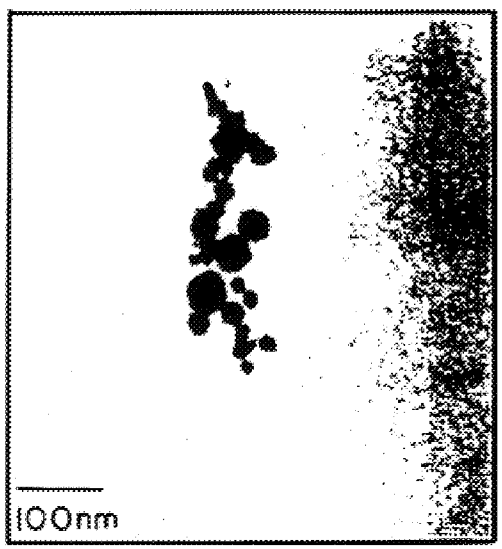
FIG. 7 is a transmission electron microscope image of the iron-titanium alloy nanopowders produced in Example 2, showing them to be in the 10–45 nanometer range.
Figure 8:
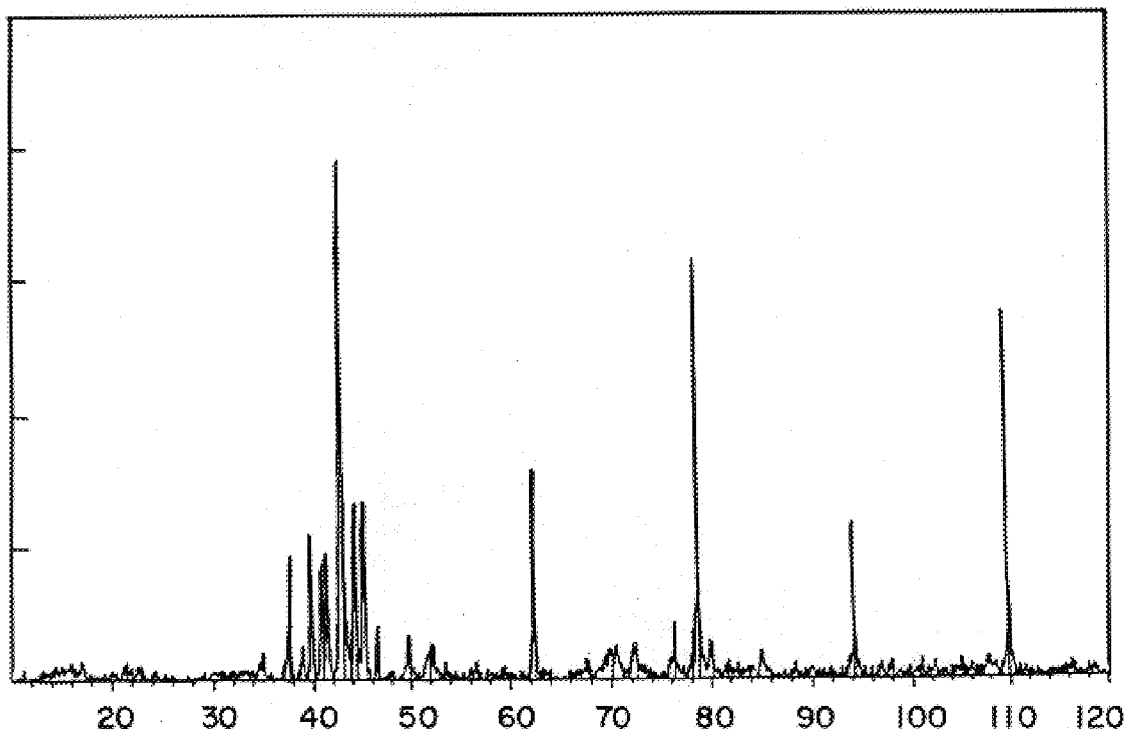
FIG. 8 is an X-ray diffraction pattern of the product of Example 2, indicating that the phases formed were titanium, iron and iron-titanium intermetallic.

Iron-Titanium Intermetallic: 2–5 micron powders of iron and 10–25 micron powders of titanium were mixed in 1:1 molar ratio and fed into the thermal reactor suspended in an argon stream (total gas flow rate, including plasma gas, was 2.75 ft$^3$/min). The reactor was inductively heated with 18 kW of RF plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 6 is the SEM micrograph of the feed powders used, showing that they were greater than 1 micrometer when fed. FIG. 7 is a TEM image of nanopowders produced by the invention, showing them to be in the 10–45 nanometer range. The size distribution was narrow, with a mean size of approximately 32 nm and a standard deviation of about 13.3 nm. Variations in the operating variables affected the size of the powder produced. The XRD pattern of the product is shown in FIG. 8, which indicates that the phases formed were titanium, iron and iron-titanium intermetallic (FeTi). The phases present illustrate that the invention can produce nanoscale powders of metals and intermetallics. To avoid condensation at the wall, argon was introduced tangentially (radial or axial injections have also been proven to be effective) at the nozzle walls. The inert gas provided cooling as well as a boundary layer to act as a barrier for any condensation on the nozzle walls.

EXAMPLE 3

Figure 9:
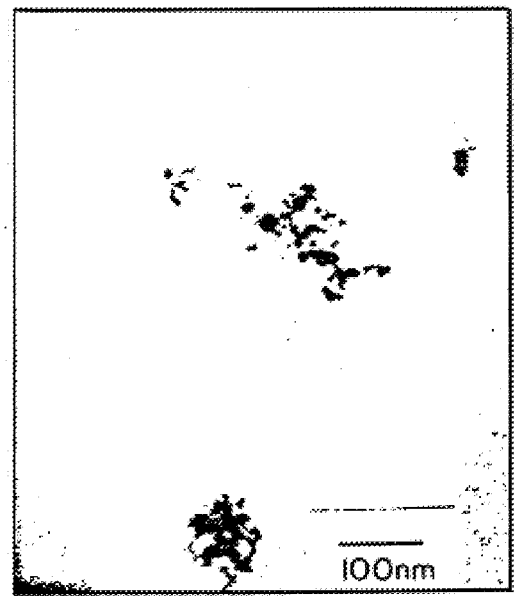
FIG. 9 is a transmission electron microscope image of the nickel aluminide nanopowder produced in Example 3.
Figure 10:
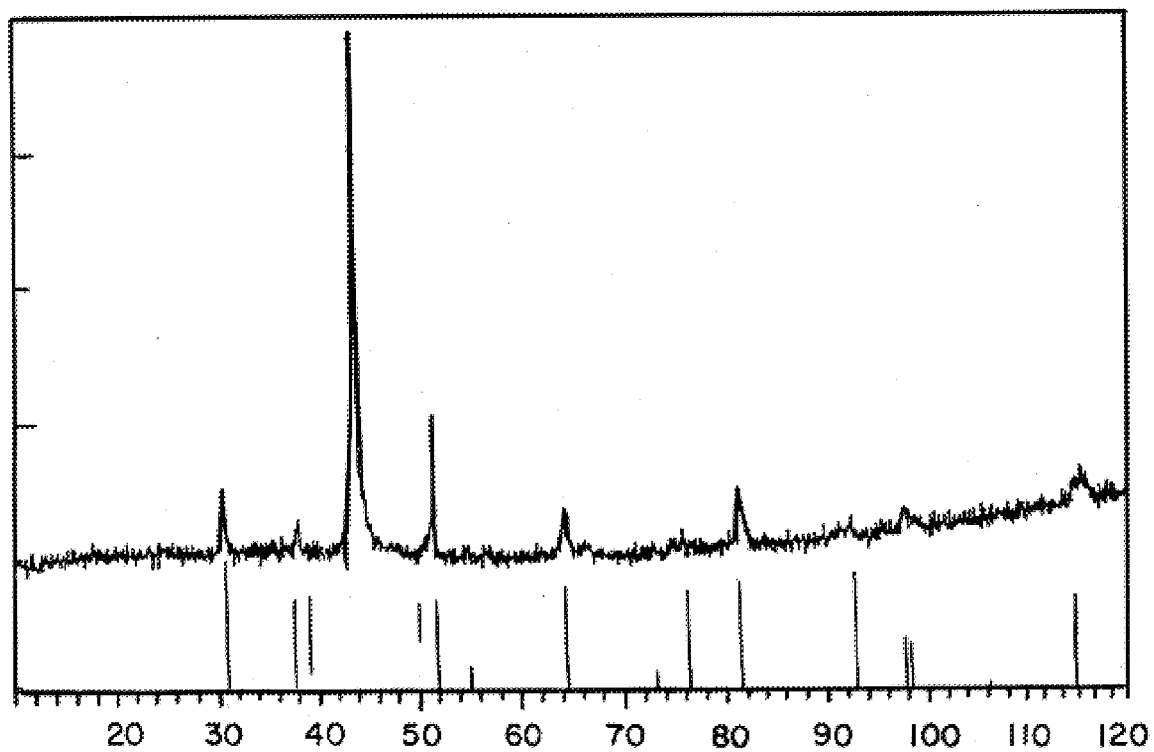
FIG. 10 is an X-ray diffraction pattern of the product of Example 3, indicating that the phase formed was NiAl.

Nickel-Aluminum Intermetallic: 1–4 micron powders of nickel and 10–30 micron powders of aluminum were mixed in 1:1 molar ratio and fed into the thermal reactor suspended in an argon stream (total feed, including plasma gas, at 2.75 ft$^3$/min). The reactor was inductively heated with 18 kW of RF plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 9 is a TEM image of the nanopowder produced by the invention, showing it to be in the 10–30 nanometer range. The size distribution was narrow, with a mean size of approximately 16.4 nm and a standard deviation of about 5.2 nm. Variations in the operating variables affected the size of the powder produced. The XRD pattern of the product is shown in FIG. 10, which indicates that the phase formed was NiAl. The phases present illustrate that the invention can produce nanoscale powders of metals and intermetallics. To avoid condensation at the wall, argon was introduced tangentially at the nozzle walls. The inert gas provided cooling as well as a boundary layer to act as a barrier for any condensation on the nozzle walls.

EXAMPLE 4

Figure 11:
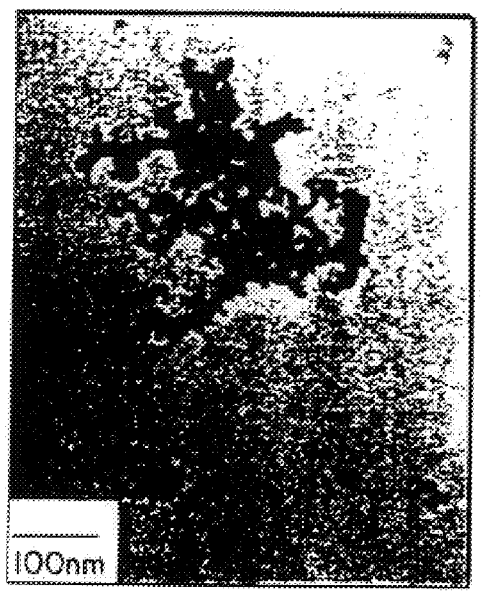
FIG. 11 is a transmission electron microscope image of the tungsten oxide nanopowder produced in Example 4.
Figure 12:
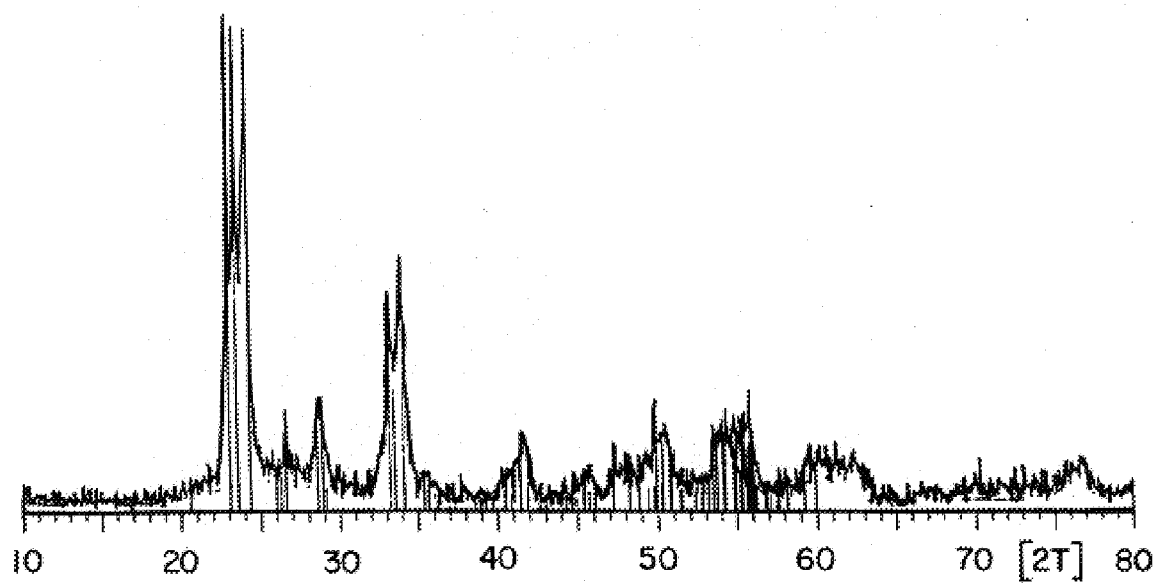
FIG. 12 is an X-ray diffraction pattern of the product of Example 4, indicating that the phase formed was $WO_3$.

Tungsten Oxide: Commercially available tungsten oxide powder (−325 mesh size) was used as the precursor to produce nanosize $WO_3$. The tungsten oxide powder was suspended in a mixture of argon and oxygen as the feed stream (flow rates were 2.25 ft$^3$/min for argon and 0.25 ft$^3$/min for oxygen). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 11 is the TEM nanograph of the $WO_3$ powder produced by the invention, showing it to be in the 10–25 nanometer range. The size distribution was narrow, with a mean size of about 16.1 nm and a standard deviation of about 6.3 nm. Variations in the operating variables (such as power input, gas pressure, gas flow rates, and nozzle throat size) affected the size of the powder produced. An XRD pattern of the product is shown in FIG. 12, which indicates that the phase present was $WO_3$. To avoid condensation at the wall, argon was introduced tangentially at the nozzle walls. The inert gas provided cooling as well as a boundary layer to act as a barrier for any condensation on the nozzle walls.

EXAMPLE 5

Figure 13:
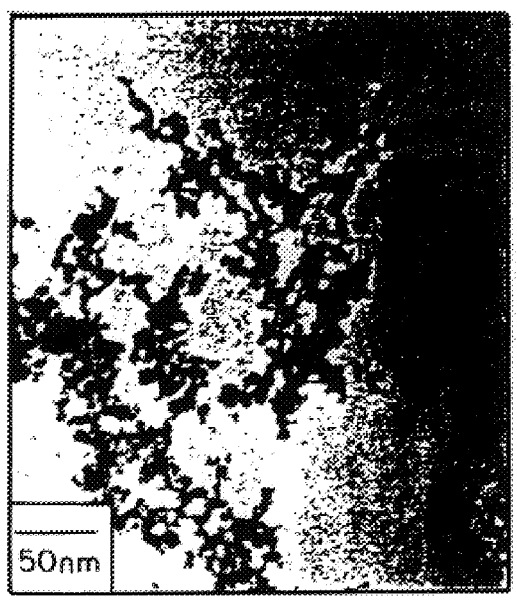
FIG. 13 is a transmission electron microscope image of the cerium oxide nanopowder produced in Example 5.
Figure 14:
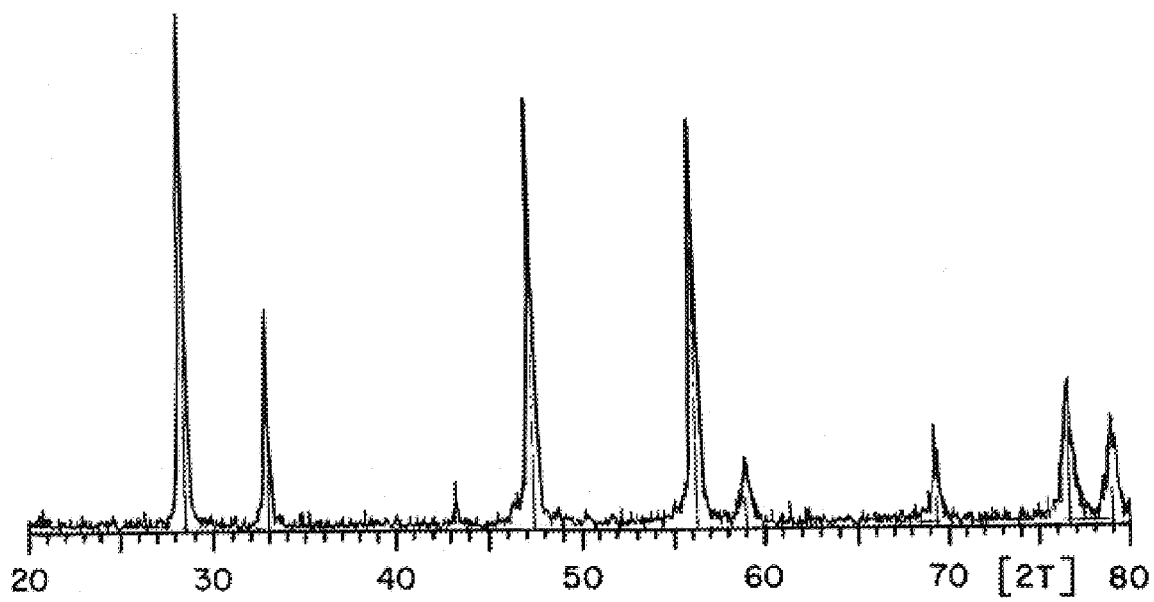
FIG. 14 is an X-ray diffraction pattern of the product of Example 5, indicating that the phase formed was $CeO_2$.

Cerium Oxide: Commercially available cerium oxide powder (5–10 micron size) was used as the precursor to produce nanosize $CeO_2$. The cerium oxide powder was suspended in a mixture of argon and oxygen as the feed stream (at total rates of 2.25 ft$^3$/min for argon and 0.25 ft$^3$/min for oxygen). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 650 Torr. The powder produced was separated from the gas by means of a cooled copper-coil-based impact filter followed by a screen filter. FIG. 13 is the TEM nanograph of the $CeO_2$ powder produced by the invention, showing it to be in the 5–25 nanometer range. The size distribution was narrow, with a mean size of about 18.6 nm and a standard deviation of about 5.8 nm. Variations in the operating variables affected the size of the powder produced. An XRD pattern of the product is shown in FIG. 14, which indicates that the phase present was $CeO_2$. To avoid condensation at the wall, argon was introduced tangentially at the nozzle walls. The inert gas provided cooling as well as a boundary layer to act as a barrier for any condensation on the nozzle walls.

EXAMPLE 6

Figure 15:
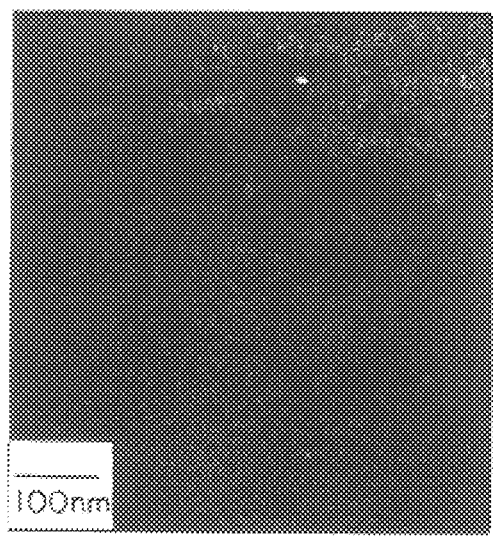
FIG. 15 is a transmission electron microscope image of the silicon carbide nanopowder produced in Example 6.
Figure 16:
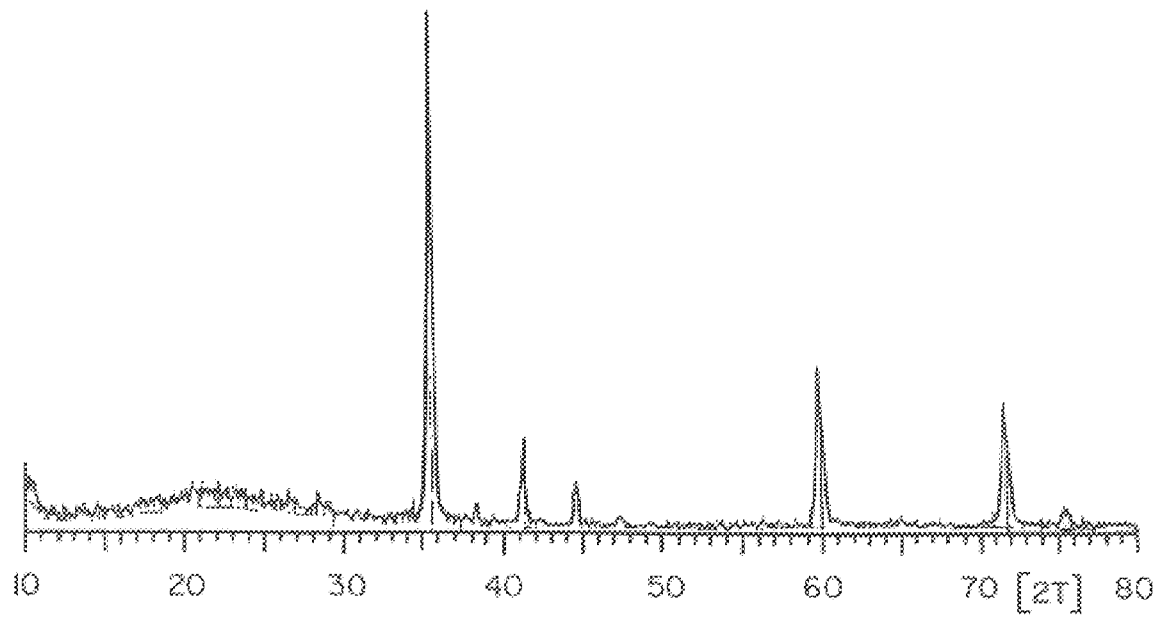
FIG. 16 is an X-ray diffraction pattern of the product of Example 6, indicating that the phase formed was SiC.

Silicon Carbide: Commercially available silicon carbide powder (−325 mesh size) was used as the precursor to produce nanosize SiC. The powder was suspended in argon as the feed stream (total argon flow rate of 2.5 ft$^3$/min). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 15 is the TEM nanograph of the SiC powder produced by the invention, showing it to be in the 10–40 nanometer range. The size distribution was narrow, with a mean size of approximately 28 nm and a standard deviation of about 8.4 nm. Variations in the operating variables affected the size of the powder produced. An XRD pattern of the product is shown in FIG. 16, which indicates that the phase present was SiC. To avoid condensation at the wall, argon was introduced tangentially at the nozzle walls. The inert gas provided cooling as well as a boundary layer to act as a barrier for any condensation on the nozzle walls.

EXAMPLE 7

Figure 17:
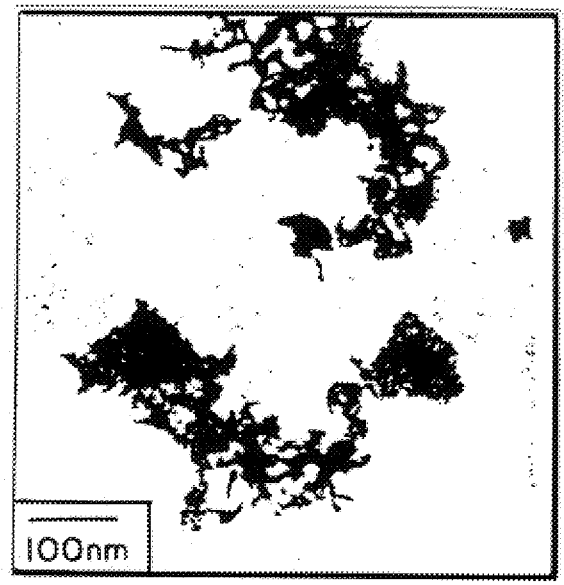
FIG. 17 is a transmission electron microscope image of the molybdenum nitride nanopowder produced in Example 7.
Figure 18:
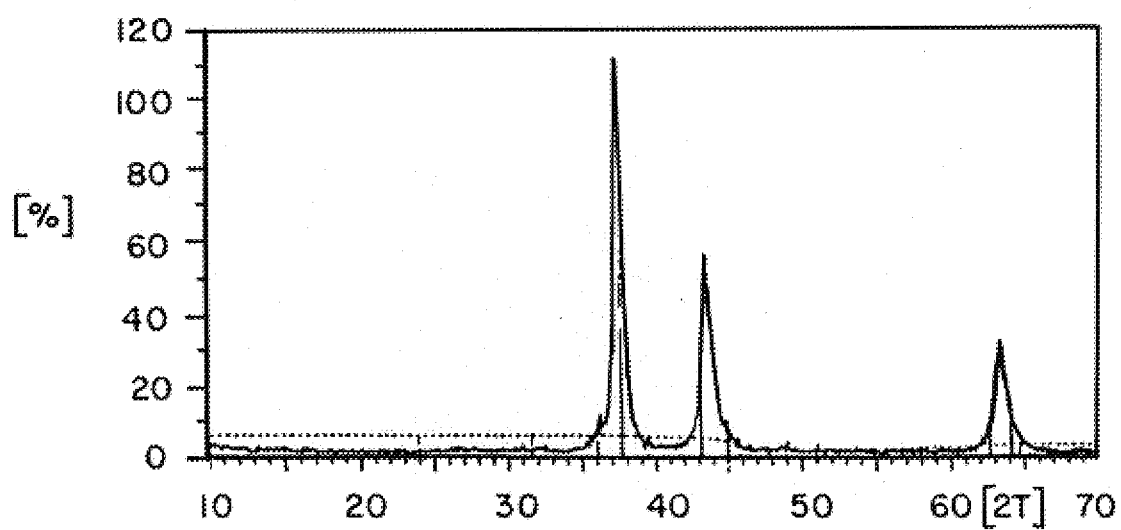
FIG. 18 is an X-ray diffraction pattern of the product of Example 7, indicating that the phase formed was $Mo_2N$.

Molybdenum Nitride: Commercially available molybdenum oxide ($MoO_3$) powder (−325 mesh size) was used as the precursor to produce nanosize $Mo_2N$. Argon was used as the plasma gas at a feed rate of 2.5 ft$^3$/min. A mixture of ammonia and hydrogen was used as the reactant gases ($NH_3$ at 0.1 ft$^3$/min; $H_2$ at 0.1 ft$^3$/min). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 17 is the TEM nanograph of the $Mo_2N$ powder produced by the invention, showing it to be in the 5–30 nanometer range. The size distribution was narrow, with a mean size of about 14 nm and a standard deviation of about 4.6 nm. Variations in the operating variables affected the size of the powder produced. An XRD pattern of the product is shown in FIG. 18, which indicates that the phase present was $Mo_2N$. To avoid condensation at the wall, argon was introduced tangentially at the nozzle walls. The inert gas provided cooling as well as a boundary layer to act as a barrier for any condensation on the nozzle walls.

EXAMPLE 8

Figure 19:
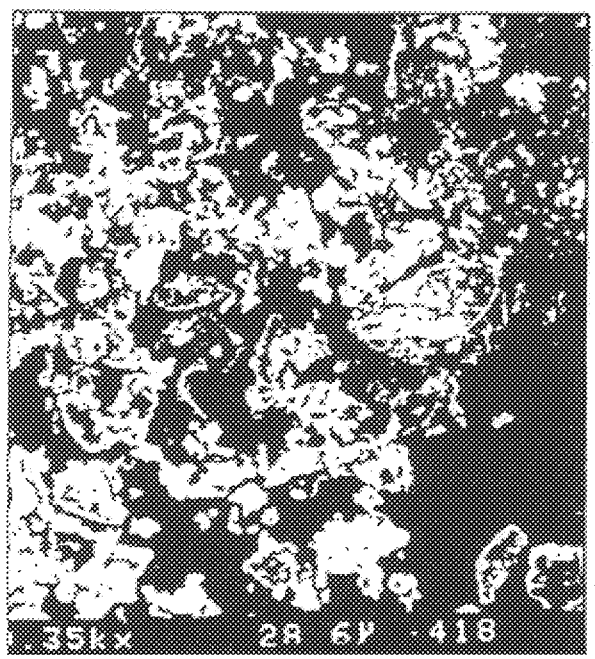
FIG. 19 is a scanning electron microscope image of the nickel boride ceramic used in Example 8, showing that the feed powder was greater than 1 micrometer.
Figure 20:
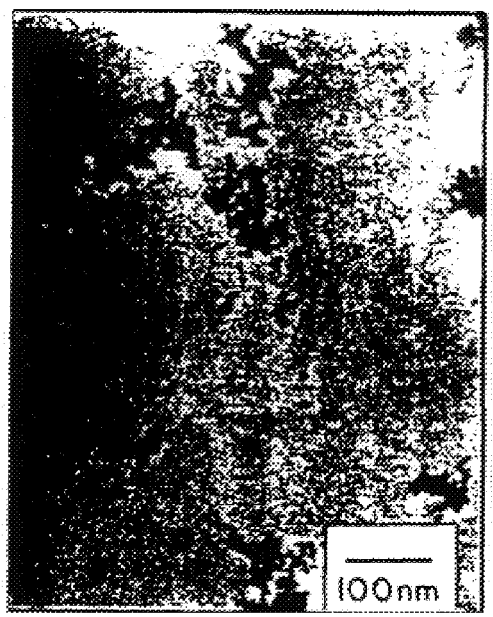
FIG. 20 is a transmission electron microscope image of the Ni and $Ni_3B$ nanopowders produced in Example 8, showing them to be in the 10–30 nanometer range.
Figure 21:
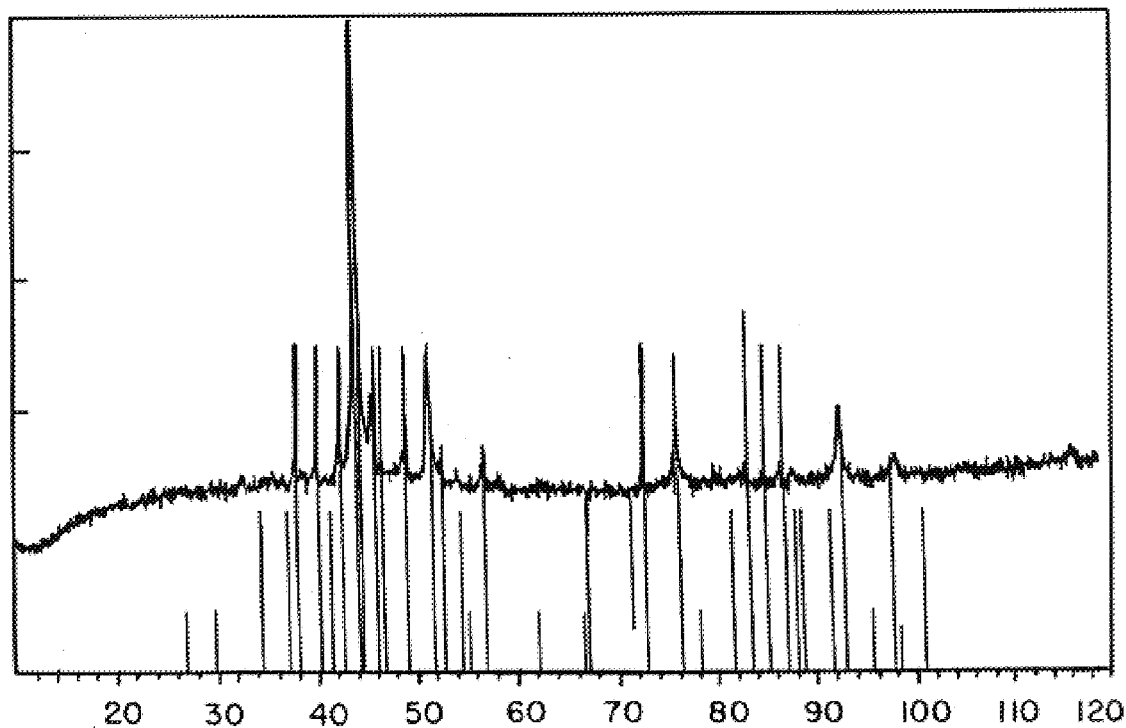
FIG. 21 is an X-ray diffraction pattern of the product of Example 8, indicating that the phases formed were Ni and $Ni_3B$.

Nickel Boride Ceramic: 10–50 micron powder of nickel boride were fed into the thermal reactor with argon (fed at a total rate, including plasma gas, of 2.75 ft$^3$/min). Once again, the reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 19 shows the SEM micrograph of the feed powders used, demonstrating that they were greater than 1 micrometer when fed. FIG. 20 is the TEM nanograph of the $Ni_3B$ powder produced by the invention, showing it to be in the 10 to 30 nanometer range. The size distribution was narrow, with a mean size of about 12.8 nm and a standard deviation of about 4.2 nm. Variations in the operating variables affected the size of the powder produced. An XRD pattern of the product is shown in FIG. 21, which indicates that the phase present were Ni and $Ni_3B$. To avoid condensation at the wall, argon was introduced tangentially at the nozzle walls. The inert gas provided cooling as well as a boundary layer to act as a barrier for any condensation on the nozzle walls.

EXAMPLE 9

Figure 22:
FIG. 22 is a transmission electron microscope image of the calcium-oxide nanopowders produced in Example 9, showing them to be in the 5–20 nanometer range.
Figure 23:
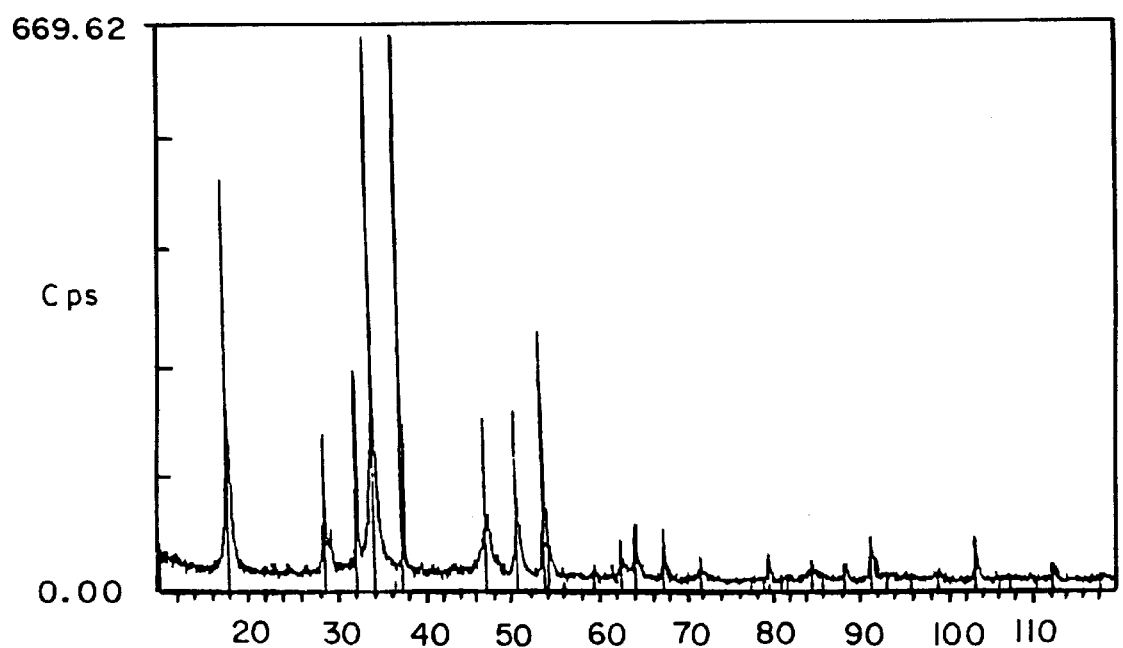
FIG. 23 is an X-ray diffraction pattern of the product of Example 9, indicating that the phase formed was CaO.

Oxide Ceramics: 5–10 micron powders of calcium carbonate were fed into the thermal reactor with argon (at 2.5 $ft^3$/min). The reactor was inductively heated with 16 kW of RF plasma to over 5,000K in the plasma zone and about 2,500K in the extended reactor zone adjacent the converging portion of the nozzle. The vaporized stream was quenched by thermal expansion to about 100 Torr. The pressure drop across the nozzle was 250 Torr, but useful results were obtained at different pressure drops, ranging from 50 to 550 Torr. The powder produced was separated from the gas by means of a cooled copper-coil-based impact filter followed by a screen filter. FIG. 22 is the TEM image of powder produced by the invention, showing it to be in the 5 to 20 nanometer range. As expected from the calcination reaction occurring in the reactor, the XRD data (shown in FIG. 23) established that the main phase of the nanopowder was CaO. Some other phases, such as $Ca(OH)_2$, were also present due to exposure to atmospheric moisture. The size distribution of the CaO was narrow, with a mean size of about 14.8 nm and standard deviation of about 3.8 nm.

An alternate run was made with $MgCO_3$ powders with mean size of about 7 microns processed with argon. Once again, nanoscale powders of MgO were produced as evidenced by TEM and XRD data. The final product powder size was observed to vary with changes in the pressure, temperature, flow rate, and compositions.

These examples demonstrate the feasibility and effectiveness of the principles of this invention in producing nanosize powders from micron-sized precursors. The process and apparatus of the invention, utilizing ultra-rapid quenching as the process step for the formation of nanopowders, provide a practical method for controlling the size of the product by manipulating process parameters. In particular, by controlling the quenching rate by changing the pressure drop over the expansion nozzle of the invention, we found that predetermined particle sizes and size distributions can be produced reliably in a continuous, steady-state process, which is easily scaleable for commercial bulk production. The process was proven viable for metals, alloys, intermetallics, ceramics, composites, and combinations thereof. In addition, we demonstrated that the process can utilize feeds of reactive components and produce submicron powders of corresponding thermodynamically-stable or metastable product species at high temperatures; that it is suitable for recycling and reusing product gases as feed gases; and for recycling and reusing any unseparated product powders as feed material. The method and apparatus of the invention solve many problems unresolved by existing processes to produce submicron powders in general and nanostructured materials in particular. Especially, the process is scaleable; it is solvent free and therefore inherently non-polluting and of low cost; it is flexible in relation to processing different feed materials; it allows simple control of product powder size and size distribution; and it does not utilize contaminating components in the feed or for processing, therefore yielding product powders that are as pure as the powders fed to the process.

Inasmuch as one of the primary inventive concepts of the invention is the effective thermal quenching and the attendant advantages produced by ultra-rapid expansion of a vaporized suspension of the feed material, it is clear that the concept could be applied as well to a system where the precursor material is in the form of a mass evaporated by any method in a low-pressure gas. Similarly, the process is applicable to liquid or gaseous precursors that are combined with one or more reactive gases in a reactor and then quenched ultra-rapidly according to the invention to produce nanosize particles with a narrow size distribution. For example, silicon tetrachloride (normally liquid at room temperature) can be reacted with methane to produce a silicon-carbide vapor which, rapidly quenched according to the invention, can produce a nanosize SiC powder. Similarly, silane ($SiH_4$, normally gaseous at room temperature) can be reacted with methane to produce a silicon-carbide vapor which can also be rapidly quenched to produce a nanosize SiC powder with a narrow size distribution. Finally, it is understood that specific changes in materials and procedures may be made by one skilled in the art to produce equivalent results.

Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A process for producing a nanoscale powder from a precursor material comprising the following steps:

evaporating the precursor material in a gaseous atmosphere in a thermal reactor so as to create a vapor/gas mixture with a temperature of at least 3000K;

initiating nucleation of the precursor material from the vapor/gas mixture prior to quenching in a zone adjacent to the thermal reactor; and quenching said vapor/gas mixture by effecting its expansion through a predetermined pressure drop, thereby causing the formation of nanoscale particles of product material in a product gas.

2. The process of claim 1, wherein said pressure drop in the quenching step is sufficient to cause a temperature of the vapor/gas mixture to change at a rate of at least 1,000° C. per second.

3. The process of claim 1, wherein said pressure drop in the quenching step is sufficient to cause a temperature of the vapor/gas mixture to change at a rate of at least 1,000,000° C. per second.

4. The process of claim 1, wherein said expansion through a predetermined pressure drop is carried out by passing the vapor/gas mixture through a converging-diverging expansion nozzle.

5. The process of claim 4, wherein said pressure drop through the converging-diverging expansion nozzle is sufficient to cause a temperature of the vapor/gas mixture to change at a rate of at least 1,000° C. per second.

6. The process of claim 4, wherein said pressure drop through the converging-diverging expansion nozzle is sufficient to cause a temperature of the vapor/gas mixture to change at a rate of at least 1,000,000° C. per second.

7. The process of claim 4, wherein said pressure drop is between 50 and 650 Torr.

8. The process of claim 1, wherein said evaporation and quenching steps are carried out on a continuous basis.

9. The process of claim 8, wherein said evaporation step is carried out by feeding said precursor material to the thermal reactor as a suspension in said gaseous atmosphere and by subjecting the suspension to an input of thermal energy.

10. The process of claim 9, wherein said thermal energy is at least partially produced by an inductive source.

11. The process of claim 9, wherein said thermal energy is at least partially produced by a microwave source.

12. The process of claim 9, wherein said thermal energy is at least partially produced by an electric arc.

13. The process of claim 9, wherein said thermal energy is at least partially produced by heat of reaction.

14. The process of claim 4, further comprising the step of providing a gaseous boundary-layer stream to form a blanket over an internal surface of the nozzle.

15. The process of claim 1, further comprising the step of coating an internal surface of said thermal reactor with a layer of said precursor material.

16. The process of claim 15, wherein said expansion through a predetermined pressure drop is carried out by passing the vapor/gas mixture through a converging-diverging expansion nozzle.

17. The process of claim 16, wherein said pressure drop through the converging-diverging expansion nozzle is sufficient to cause a temperature of the vapor/gas mixture to change at a rate of at least 1,000° C. per second.

18. The process of claim 15, further comprising the step of providing a gaseous boundary-layer stream to form a blanket over an internal surface of the nozzle.

19. The process of claim 1, further comprising the step of separating said nanoscale particles of product material from said product gas.

20. The process of claim 19, further comprising the step of recycling said product gas by feeding the product gas to the thermal reactor with said precursor material.

21. A process for producing a nanoscale powder from a precursor material comprising the following steps:
   reacting the precursor material with a reactive component in a thermal reactor so as to create a vapor/gas mixture with a temperature of at least 3000K;
   initiating nucleation of the precursor material from the vapor/gas mixture prior to quenching in a zone adjacent to the thermal reactor and;
   quenching said vapor/gas mixture by effecting its expansion through a predetermined pressure drop, thereby causing formation of nanoscale particles of a product material in a product gas.

22. The process of claim 21, wherein said expansion through a predetermined pressure drop is carried out by passing the vapor/gas mixture through a converging-diverging expansion nozzle.

23. The process of claim 22, wherein said pressure drop through the converging-diverging expansion nozzle is sufficient to cause a temperature of the vapor/gas mixture to change at a rate of at least 1,000° C. per second.

24. The process of claim 21, wherein said evaporation and quenching steps are carried out on a continuous basis.

25. The process of claim 22, further comprising the step of providing a gaseous boundary-layer stream to form a blanket over an internal surface of the nozzle.

* * * * *